United States Patent
Lang et al.

(10) Patent No.: US 6,433,152 B1
(45) Date of Patent: Aug. 13, 2002

(54) SOPHOROSELIPIDS, METHOD FOR THEIR PRODUCTION AND USE

(75) Inventors: Siegmund Lang; Andreas Brakemeier, both of Braunschweig; Dieter Wullbrandt; Andreas Seiffert-Störicko, both of Hofheim, all of (DE)

(73) Assignee: Aventis Research & Technologies GmbH & Co KG (DE)

( * ) Notice: Subject to any disclaimer, the term of this patent is extended or adjusted under 35 U.S.C. 154(b) by 0 days.

(21) Appl. No.: 09/530,769

(22) PCT Filed: Oct. 17, 1998

(86) PCT No.: PCT/EP98/06590

§ 371 (c)(1),
(2), (4) Date: Jul. 3, 2000

(87) PCT Pub. No.: WO99/24448

PCT Pub. Date: May 20, 1999

(30) Foreign Application Priority Data

Nov. 7, 1997 (DE) .......................................... 197 49 413

(51) Int. Cl.$^7$ .......................... C07G 3/00; C07H 15/00; C07H 17/00; C07H 13/02; C07H 15/04
(52) U.S. Cl. ..................... 536/18.5; 536/18.6; 536/119; 536/120; 536/123.1; 536/123.13; 536/124
(58) Field of Search ............................... 536/18.5, 18.6, 536/119, 120, 123.1, 123.13, 124

(56) References Cited

U.S. PATENT DOCUMENTS 4,215,213 A 7/1980 Inoue et al. ................. 536/115
5,767,255 A 6/1998 Wulbrand et al. ......... 536/18.5

FOREIGN PATENT DOCUMENTS

EP 0745608 12/1996

OTHER PUBLICATIONS

Gorin et al., "Hydroxy Fatty Acid Glycosides of Sophorose From Torulopsis Magnoliae" *Can J. Chem.* vol. 39: pp. 846–854 (1961).

Kirchner et al., "Resolution of Racemic Mixtures via Lipase Catalysis in Organic Solvent" *J. Am. Chem. Soc.*, 107: pp. 7072–7076 (1985).

Hommel, R.K., "Formation and Physiological role of Biosurfactants produced by hydrocarbon–utilizing microorganisms" *Biodegradation*, 1, pp. 107–119 (1990).

(List continued on next page.)

*Primary Examiner*—Jezia Riley
(74) *Attorney, Agent, or Firm*—Connolly Bove Lodge & Hutz LLP

(57) ABSTRACT

The invention relates to sophoroselipids of formula (I) wherein $R^4$ represents H, —$CH_2CH_3$, —$CH_2CH_2CH_3$, n is an integer number from 2 to 27, $R^1$ and $R^2$ represent, independently from each other, H or a group of formula (II), and $R^3$ represents H or —OH. The invention also relates to a method for producing sophoroselipids of formula (I) wherein $R^1$, $R^2$, $R^3$ and n have the aforementioned meanings and $R^4$ represents —$CH_3$, —$CH_2CH_3$ or —$CH_2CH_2CH_3$. According to this method, a yeast capable of secreting a sophoroselipid in the form of a lactone in the culture excess, is fermented in a culture medium containing a glycerin. a succinate, a mono-, di- and/or tri-saccharide and a lipid precursor, said sophoroslipid being then isolated from the culture solution. The inventive method is characterised in that the lipid precursor contains one or more 3-alkanols, 4-alkanols or an alkanone with a chain length from 6 to 30 carbon atoms or mixtures of said alkanoistalkanone. Furthermore, according to a variant of the aforementioned method for producing sophoroselipids of formula (I), wherein $R^1$, $R^2$, $R^3$ and n have the meanings aforementioned and $R^4$ represents —$CH_3$, —$CH_2CH_3$ or —$CH_2CH_2CH_3$, the culture medium is maintained during fermentation under a reduced oxygen concentration. The new sophoroselipids may be used, e.g., as surfactants, cosmetics, disinfecting agents or pharmaceutical products.

15 Claims, 1 Drawing Sheet

OTHER PUBLICATIONS

Jones et al., "Microbiological Oxidation of Long–chain Aliphatic Compounds. Part 1. Alkanes and Alk–1–enes" *J. Chem. Soc.*, (C), pp. 2801–2808 (1968).

Davila et al., "Sophorose lipid production from lipidic precursors: predictive evaluation of industrial substrates" *Journal of Industrial Microbiology*, 13, pp. 249–257 (1994).

Hallgren, C., et al, *Carbohydrate Research 260*:63–71, XP–002106415 (1994).

Pozsgay, V., et al, *Carbohydrate Research 277*:51–66, XP–002106416 (1995).

Yuda, M., et al, *Phytochemistry 29*:1989–1993, XP–002106417 (1990).

Morikawa, K., et al, *Chemical Abstracts 126*:118152z, XP–002106418 (1997).

Brakemeier, A., et al, *Biotechnology Letters 17*:1183–1188, XP_000566808 (1995).

Matsumura, S., et al, *J. of the Japan Oil Chemists' Society: 40*: 709–714, XP–000653016 (1991).

SOPHOROSELIPIDS, METHOD FOR THEIR PRODUCTION AND USE

The present invention relates to novel sophorose lipids, methods for their biotechnological production and their use as surfactant, cosmetics, disinfectant or pharmaceuticals.

BACKGROUND OF THE INVENTION

Microbial glycolipids have been known for some years as biosurfactants with versatile applications in cosmetics, the detergent and cleaner sector, the foodstuff sector, medicine and environmental protection. Compared with chemical surfactants, because of their biological origin they have advantages such as, for example, lower toxicity and generally better degradability. They are produced by bacteria, yeasts or fungi when grown on long-chain petroleum products, on vegetable oils and fats or derivatives thereof, or on mono- and oligosaccharides. Targeted modification of the molecular structures of these products by altering the carbon source has to date been possible to only a slight extent. Since its discovery in 1961, sophorose lipid has been among the intensively researched microbial glycolipids [P. A. Gorin, J. F. T. Spencer and A. P. Tulloch; Can. J. Chem. 39 (1961), 846–855].

According to various reports, sophorose lipid can be produced by various yeasts of the genus Candida (Torulopsis) as secondary metabolite using a substrate from the carbon sources indicated above. Suitable yeast strains described are *Candida bombicola, Candida bogoriensis, Candida magnoliae, Candida gropengiesser* and *Candida apicola* [R. Hommel, Biodegradation, 1, (1991), 107].

The sophorose lipids produced by the genus Candida have a structure depicted below (1).

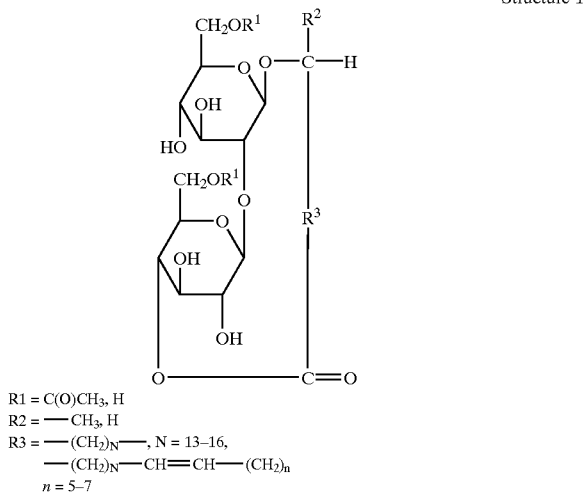

Structure 1

R1 = C(O)CH₃, H
R2 = —CH₃, H
R3 = —(CH₂)ₙ—, N = 13–16,
    —(CH₂)ₙ—CH═CH—(CH₂)ₙ
    n = 5–7

Besides this main lactone product with a hydroxy fatty acid which is linked both glycosidically and in the manner of an ester, also found in small amounts are uncyclized intermediates. Depending on the substrate employed, the hydroxy fatty acid can be saturated, mono- or else polyunsaturated. Furthermore, the 6'-O and 6"-O positions of the glucose units are acetylated to varying extents. Only slight differences in the fatty acids in the side chain of the sophorose lipids are found.

To produce a glycolipid with amphiphilic structure, i.e. high surface activity, the sophorose lipid lactones must be converted into the sophorose lipid esters or amides by elaborate synthetic and purification stages [S. Inoue, et al. U.S. Pat. No. 4,215,213, 1990; Y. Ishigami, JP-Application: Toku Kai Hei 6-100581].

It is known that on fermentation of yeasts of the genus Candida using 2-alkanols, in place of vegetable oils and fats, fatty acids or their alkyl esters, it is. possible to obtain uncyclized glucose lipids and sophorose lipids with surface-active properties (see DE 195 18 982.5). The corresponding 2-alkanols are, however, costly or else elaborate to produce. It has not to date been possible to use more cost-effective and more easily obtainable 1-alcohols because it is known that they are to a large extent converted into the corresponding acids before they are transformed into glycolipids (see, for example, D. F. Jones, R. Howe, J.Chem.Soc. -C-, (1968), 2801–2808). There have merely been indications of how to obtain these substances, which have never been isolated or characterized in detail (Davila, A.-M., Marchal, R., Vandecasteele, J.-P., J. lndustr. Microbiol., (1994) 249–257).

SUMMARY OF THE INVENTION

It has now been found, surprisingly, that uncyclized glucose lipids and sophorose lipids with surface-active properties are also obtainable on use of 3-alkanols, 4-alkanols, 2-alkanones, 3-alkanones and 4-alkanones.

In addition, successful use of 1-alcohols and alkanals for obtaining the novel products is possible when the culture medium has a reduced oxygen concentration during fermentation of the microorganisms.

The invention thus relates to compounds of the formula I

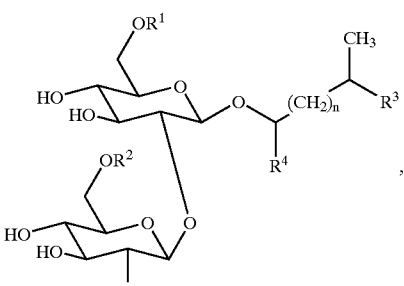

I in which

| | | |
|---|---|---|
| $R^4$ | is H, -CH₂CH₃, -CH₂CH₂ CH₃, | $\begin{matrix} O \\ \| \\ C \\ \| \\ CH_3 \end{matrix}$ |
| n | is an integer from 2 to 27, | |
| $R^1$ and $R^2$ | are, independently of one another, H or and | |
| $R^3$ | is H or -OH. | |

DESCRIPTION OF THE PREFERRED EMBODIMENTS

Figure 1:
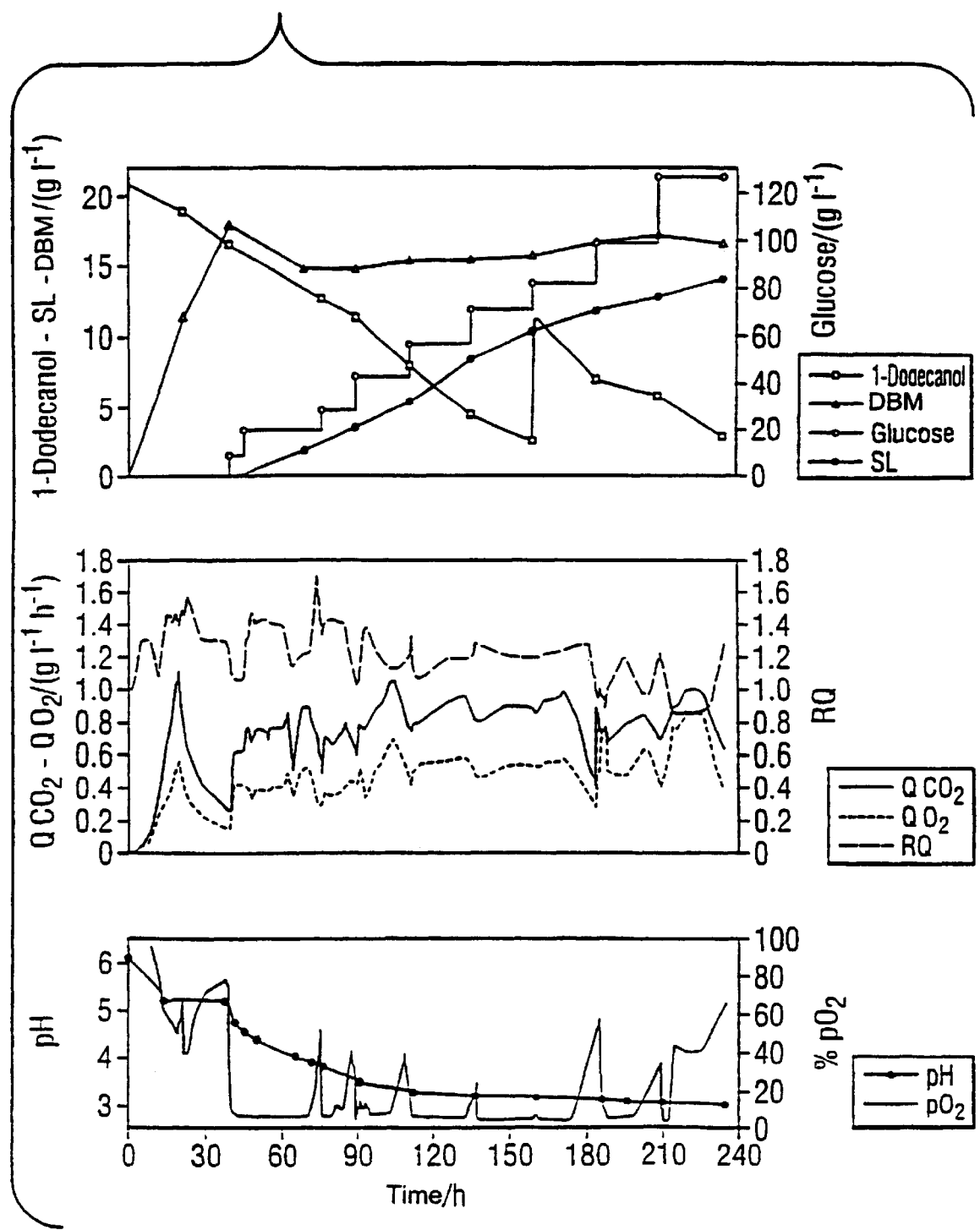
FIG. 1 summarizes the progress of the bioreactor cultivation on the basis of all the analytical parameters.

Preferred embodiments of the present invention are described below.

1. A compound of the formula I in which $R^4$ is H, where $R^1$ and $R^2$ together are —C(O)CH₃,
   $R^1$ is H and $R^2$ is —C(O)CH₃, $R^1$ is —C(O)CH$_3$ and $R^2$ is H or $R^1$ and $R^2$ are H, $R^3$ is H and where n is an integer from 6 to 14, preferably 8 to 12.

2. A compound of the formula I in which $R^4$ is —CH$_2$CH$_3$ or —CH$_2$CH$_2$CH$_3$, where $R^1$ and $R^2$ together are —C(O)CH$_3$, $R^1$ is H and $R^2$ is —C(O)CH$_3$, $R^1$ is —C(O)CH$_3$ and $R^2$ is H or $R^1$ and $R^2$ are H, $R^3$ is H or —OH, and where n is an integer from 6 to 14, preferably 8 to 12.

The present invention further relates to a method for producing sophorose lipids according to the formula I, where the radicals $R^1$, $R^2$ and $R^3$ and n have the abovementioned meaning, and $R^4$ is —CH$_3$, —CH$_2$CH$_3$ or —CH$_2$CH$_2$CH$_3$, in which a yeast with the ability to secrete sophorose lipids in the form of a lactone into the culture supernatant is fermented in a culture medium which contains glycerol, succinate, a mono-, a di- and/or a trisaccharide and a lipid precursor, and then the sophorose lipid is isolated from the culture solution, wherein the lipid precursor comprises one or more 3-alkanols, 4-alkanols or alkanones with a chain length of from 6 to 30 carbon atoms or mixtures of these alkanols/alkanones.

The chain length of the alkanol/alkanone is preferably 10 to 18 carbon atoms, with which it is possible to produce a compound of the formula I in which n is an integer from 4 to 14, and the alkanone particularly preferably employed is 2-dodecanone or 3-dodecanone, which makes it possible to produce a compound of the formula I with n=8 and $R^4$=—CH$_3$ or with n=7 and $R^4$=—CH$_2$CH$_3$, where $R^1$, $R^2$ and $R^3$ have the abovementioned meaning.

The present invention further relates to a method for producing sophorose lipids according to the formula I, where the radicals $R^1$, $R^2$ and $R^3$ and n have the abovementioned meaning, and $R^4$ is H, —CH3, —CH$_2$CH$_3$ or —CH$_2$CH$_2$CH$_3$, in which a yeast with the ability to secrete sophorose lipids in the form of a lactone into the culture supernatant is fermented in a culture medium which contains glycerol, succinate, a mono-, a di- and/or a trisaccharide and a lipid precursor, and then the sophorose lipid is isolated from the culture solution, wherein the lipid precursor comprises one or more alkanols, alkanals or alkanones with a chain length of from 6 to 30 carbon atoms or mixtures of these alkanols/alkanals alkanones, and the culture medium is kept under a reduced oxygen concentration during the fermentation.

The chain length of the alkanol/alkanone/alkanal is preferably from 10 to 18 carbon atoms, which makes it possible to produce a compound of the formula I in which n is an integer from 4 to 15; a 1-alkanol or an alkanal is preferably used as lipid precursor, and 1-dodecanol is particularly preferably employed as alkanol, which makes it possible to produce a compound of the formula I with n=9 and $R^4$=H, where $R^1$, $R^2$ and $R^3$ have the abovementioned meaning.

Lipid precursor means in this connection compounds which comprise an alkyl chain of from 6 to 30 carbon atoms and as functional group at least one hydroxyl and/or one carbonyl group.

Lipid precursor examples are 1-alkanols, 2-alkanols, 3-alkanols, 4-alkanols, alkanals, 2-alkanones, 3-alkanones, 4-alkanones with a chain length of from 6 to 30 carbon atoms.

Examples of 1-alkanols are, without intending a restriction hereby, 1-hexanol, 1-octanol, 1-decanol, 1-undecanol, 1-dodecanol, 1-tetradecanol, 1-pentadecanol, 1-octadecanol, 1-eicosanol or 1-triacontanol, with 1-dodecanol and 1-tetradecanol being preferred.

Examples of 2-alkanols are, without intending a restriction hereby, 2-hexanol, 2-octanol, 2-decanol, 2-undecanol, 2-dodecanol, 2-tetradecanol, 2-pentadecanol, 2-octadecanol, 2-eicosanol or 2-triacontanol, with 2-dodecanol and 2-tetradecanol being preferred.

Examples of 3-alkanols are, without intending a restriction hereby, 3-hexanol, 3-octanol, 3-decanol, 3-undecanol, 3-dodecanol, 3-tetradecanol, 3-pentadecanol, 3-octadecanol, 3-eicosanol or 3-triacontanol, with 3-dodecanol and 3-tetradecanol being preferred.

Examples of 4-alkanols are, without intending a restriction hereby, 4-octanol, 4-decanol, 4-undecanol, 4-dodecanol, 4-tetradecanol, 4-pentadecanol, 4-octadecanol, 4-eicosanol or 4-triacontanol, with 4-dodecanol and 4-tetradecanol being preferred.

Examples of alkanals, are, without intending a restriction hereby, hexanal, octanal, decanal, undecanal, dodecanal, tetradecanal, pentadecanal, octadecanal, eicosanal or triacontanal, with dodecanal and tetradecanal being preferred.

Examples of 2-alkanones are, without intending a restriction hereby, 2-hexanone, 2-octanone, 2-decanone, 2-undecanone, 2-dodecanone, 2-tetradecanone, 2-pentadecanone, 2-octadecanone, 2-eicosanone or 2-triacontanone, with 2-dodecanone and 2-tetradecanone being preferred.

Examples of 3-alkanones are, without intending a restriction hereby, 3-hexanone, 3-octanone, 3-decanone, 3-undecanone, 3-dodecanone, 3-tetradecanone, 3-pentadecanone, 3-octadecanone, 3-eicosanone or 3-triacontanone, with 3-dodecanone and 3-tetradecanone being preferred.

Examples of 4-alkanones are, without intending a restriction hereby, 4-octanone, 4-decanone, 4-undecanone, 4-dodecanone, 4-tetradecanone, 4-pentadecanone, 4-octadecanone, 4-eicosanone or 4-triacontanone, with 4-dodecanone and 4-tetradecanone being preferred.

The extent of the formation of the novel structural type resulting in particular on use of 1-alkanols/alkanals is linked to a restriction of the oxygen supply during the production phase. Limitation of the oxygen concentration in the culture medium by means of suitable methods makes it possible virtually to prevent the yield-minimizing oxidation of the fatty alcohol to the fatty acid and thus brings about increased formation of the required products.

Suitable methods for limiting the oxygen concentration are, for example, without intending a restriction hereby, a reduction in the gas-introduction rate and decreasing the stirrer speed, it also being possible for the oxygen depletion to be brought about by the metabolism of the yeasts. The oxygen concentration can be obtained by measuring the oxygen partial pressure. This is 5 to 40%, preferably 5 to 15%, of the saturation value during the product formation phase of the fermentation. The saturation value relates to air (oxygen content about 21% based on the volume of the gas mixture) which is passed through the culture solution under atmospheric pressure at the particular fermentation temperature. It can be determined with a suitable probe at the start of the fermentation.

It is possible in the method according to the present invention to ferment all yeast strains which secrete the sophorose lipids described in the literature in lactone form (Structure 1) into the culture supernatant.

A particularly suitable yeast for the method according to the invention is one of the genus Candida, and the commercially available *Candida bombicola, Candida bogoriensis, Candida magnoliae, Candida gropengiesseri* or *Candida apicola* is preferably fermented.

Particularly suitable as carbon source are glucose or sucrose.

The invention is described in detail below. It is also defined by the contents of the patent claims.

The use of alkanols, alkanals or alkanones with chain lengths of from C6 to C30 as hydrophobic carbon source in addition to another carbon source such as, for example, glycerol, succinate or mono-, di- and trisaccharides such as, for example, sucrose, mannose, fructose, glucose, and D-mannitol or other sugar alcohols, preferably glucose or sucrose, results in the isolation of sophorose lipids with variation in the structure of the hydrophobic part of the molecule. The purified products in each case contain predominantly lipid components with the chain length of the substrate employed in each case, with the latter either being directly incorporated into the glycolipid (compounds of structures 2 with $R^3$=H) or being linked, after ($\omega$-1) hydroxylation as alkanediol via a glycosidic linkage to the sugar component (compounds of structure 3 with $R^3$=OH).

Exclusively nonionic surfactants with a typical surfactant structure are produced in this way.

The products are un-, mono- or diacetylated in the 6'-O and 6"-O positions of the glucose unit in the sugar part. It is possible to obtain compounds, corresponding to structures 2 and 3, in each case with n=2 to 27, by varying the chain length of the alkanols or alkanalsialkanones (C6 to C30) employed. The acetylated sophorose lipids can be converted into the unacetylated compounds by alkaline hydrolysis.

Accordingly, it is possible to produce for example on use of 1-hexanol a compound of the formula I with n=3, 1-octanol a compound of the formula I with n=5, 1-decanol a compound of the formula I with n=7, 1-undecanol a compound of the formula I with n=8, 1-dodecanol a compound of the formula I with n=9, 1-tetradecanol a compound of the formula I with n=11, 1-pentadecanol a compound of the formula I with n=12, 1-octadecanol a compound of the formula I with n=15, 1-eicosanol a compound of the formula I with n=17 or on use of 1-triacontanol a compound of the formula I with n=27, where $R^1$, $R^2$, $R^3$ and $R^4$ have the meaning indicated above.

The 1-alkanols, the 3-alcohols and the 4-alcohols, and the alkanals, 2-alkanones, 3-alkanones and 4-alkanones of chain length C6 to C30 can mostly be purchased, and some of them can be prepared from the appropriate alkenes which can be bought. The alcohols can furthermore be obtained from the alkanones and the aldehydes (Organikum, 16th Edition, VEB-Deutscher Verlag der Wissenschaften 1986 or other appropriate textbooks of practical organic chemistry).

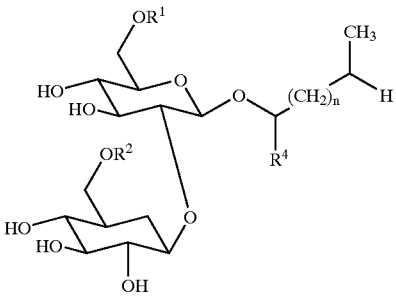

Structure 2

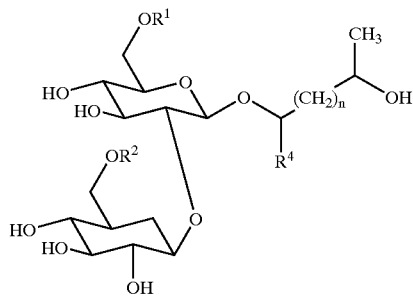

Structure 3

2, 3:n=2–27; $R^1$, $R^2$=H or —C(O)CH$_3$;
$R^4$=H, CH$_3$, CH$_2$CH$_3$, CH$_2$CH$_2$CH$_3$

2a: n=9; $R^1$, $R^2$=—C(O)CH$_3$; $R^4$=H (Compound 1, see Example 1)

2b: n=9; $R^1$, $R^2$=H; $R^4$=H (Compound 2, see Example 3)

To isolate the sophorose lipids of Structures 2 and 3 which have been formed, the culture solution after removal of the biomass by centrifugation or filtration is neutralized with an alkali and exhaustively extracted with an organic solvent such as, for example, carboxylic acid such as ethyl acetate, butyl acetate or ether such as tert-butyl methyl ether and diethyl ether or other solvents known to the skilled worker. The organic phases are separated off, combined and dried over a dessicant, such as, for example, sodium sulfate. Removal of the extract in vacuo and azeotropic removal of the water result in a yellowish brown crude product.

Alkaline hydrolysis with alkalis (for example aqueous NaOH) or alkanolates (for example sodium methanolate) can be used to convert the products acetylated in the 6'-O and 6"-O positions into the corresponding hydroxyl compounds.

The producer strains employed are fermented in a medium containing alkanols, alkanals or alkanones with a chain length of from C6 to C30, preferably C10 to C18. The concentration of alkanols, alkanals or alkanones can be adjusted at the start of the fermentation or chosen to accord with the conversion rate by continuous replenishment, preference being given to replenishment. It has proven suitable to use sugars, preferably glucose or sucrose, to provide an additional carbon source. The medium should, besides the carbon source, also contain one or more nitrogen sources, sulfate and magnesium, and potassium, sodium, calcium and chloride ions, one or more phosphate sources, and a complex substrate promoting growth, such as, for example, yeast extract.

The sugar is used in concentrations of from 30 to 200 g/l of nutrient solution, preferred concentrations being between 80 and 150 g/l.

It is possible to use as nitrogen source the nitrogen sources known to the skilled worker, such as, for example, urea, ammonium chloride or ammonium sulfate, in concentrations of from 0.1 to 5 g/l of nutrient solution, with a concentration of 0.5–2.5 g/l preferably being chosen.

Employed as phosphorus source and for buffering the medium is a 0.001 to 0.1 molar sodium phosphate or potassium phosphate buffer or a mixture of the two metal ions.

The optimal temperature for the fermentation is in the range between 20 and 40° C., preferably 25 to 30° C.

The pH is not controlled and falls during the fermentation. It is adjusted at the start of the fermentation to a value of about 5 to 7, preferably 5.5 to 6.5, by the buffer. The pH during the product formation phase is preferably in the range from 2.5 to 4.

The sophorose lipids obtained as explained above have a distinctly increased solubility (alcohol chain length <C22) compared with conventional products while reducing the surface tension of water to a greater extent.

It is possible through the use of primary alcohols, aldehydes and ketones to reduce considerably the costs of the products so that they can be employed for applications for which products obtainable from 2-alcohols are too costly.

The novel sophorose lipids have an excellent surface activity and interfacial activity. Their biodegradability is very good and they have a bactericidal effect.

The products can be used as surfactants, emulsifiers, cosurfactants and as moisture-storing agents. They therefore have prospective applications in the detergent and cleaner sector. Since they have low toxicity they can be used to produce cosmetics and be employed in the foodstuff sector. As biodegradable biosurfactants they can be used in environmental protection. Because of their microbicidal effect they can be used in medicine, for example as pharmaceuticals or as disinfectants.

It is moreover possible to obtain enantiomerically pure alcohols from the biosurfactant. The microorganisms convert the employed ketones or racemic secondary alcohols into optically active alcohols. The enantiomeric excess achieved is considerably higher than 95%.

Liberation of the optically active alcohols is possible, for example, without intending a restriction hereby, by acidic methanolysis.

The invention is explained in detail hereinafter by means of exemplary embodiments.

EXAMPLE 1

To produce dodecyl sophoroside, 100 ml of a culture medium of the following composition is introduced into a 500 ml Erlenmeyer flask with baffles:

| | |
|---|---|
| Glucose.$H_2O$ | 150.00 g/l |
| Sodium citrate.3 $H_2O$ | 5.00 g/l |
| Yeast extract (granulated, Merck, Darmstadt) | 4.00 g/l |
| Ammonium chloride | 1.54 g/l |
| Potassium dihydrogen phosphate | 1.00 g/l |
| Magnesium sulfate.7 $H_2O$ | 0.70 g/l |
| Sodium chloride | 0.50 g/l |
| Calcium chloride.2 $H_2O$ | 0.27 g/l |
| Dipotassium hydrogen phosphate.3 $H_2O$ | 0.16 g/l |

The medium is inoculated with the yeast *Candida bombicola* ATCC 22214 and incubated on a rotary shaker at 100 rpm at a temperature of 30° C. After a cultivation time of 48, 72 and 96 h, in each case 5 g/l 1-dodecanol are added under aseptic conditions to the culture solution. The culture is carried out under unchanged conditions between and after the additions of the alcohol. The measured dry biomass concentration when cultivation is stopped is 17 g/l. The pH of the culture suspension decreases over the entire range of cultivation. After a cultivation period of 10 d, the supplied amount of alcohol is converted; the cultivation is then stopped.

To isolate the products, the culture suspension is neutralized with 1N sodium hydroxide solution and then extracted twice with twice the volume of ethyl acetate. The organic phases are separated off, combined and dried over anhydrous sodium sulfate. After removal of the desiccant on a paper filter, the solvent is removed by distillation under reduced pressure in a rotary evaporator. The solidified, virtually anhydrous, yellowish brown crude product is obtained in a yield of 8 g/l, corresponding to 0.53 g per g of 1-dodecanol.

Besides the dodecyl sophorosides (Compound 1: formula I in which n=9; $R^1$, $R^2$=—C(O)$CH_3$; $R^3$=H and $R^4$=H (molecular structure 2a) and Compound 2: formula I in which n=9; $R^1$, $R^2$=H; $R^3$=H and $R^4$=H (molecular structure 2b)), it also contains small amounts of the sophorose lipid lactone and can be separated by thin-layer chromatography on silylated silica gel (RP-18) with the eluent mixture methanol/water 90:10 (v/v) into its individual substances with characteristic $R_f$ values.

It can be proven by nuclear magnetic resonance spectroscopy and FAB mass spectrometry, and by combined gas chromatographic/mass spectrometric analysis of the hydrophobic part of the molecule (after acidic methanolysis) of the compounds that the individual compounds have the basic molecular structures depicted in the figures. The main product of the cultivation is Compound 1 (molecular structure 2a).

$R_f$(RP-18: methanol/water 90:10 v/v) 0.46 [Compound 1]

Spectroscopic Data for Compound 1

MS (FAB, matrix glycerol, neg.):

m/z=593 (100, [M−H]⁻), 551 (30, [M−$COCH_3$]⁻, 509 (6, [M−2 $COCH_2$−H]⁻)

Characterization of the Product Mixture on the Basis of the Relative Amounts of its Lipid Components by GC-MS (FA=Fatty Acid)

| Glycolipid mixture based on glucose/1-dodecanol: | |
|---|---|
| 1-dodecanol | 69.8% |
| FA C 12:0 | 10.0% |
| FA 15-OH-C 16:0 | 1.1% |
| FA 16-OH-C 16:0 | 1.4% |
| FA 17-OH-C 18:1 | 8.3% |
| FA 17-OH-C 18:0 | 5.5% |
| FA 18-OH-C 18:1 | 1.6% |
| FA 18-OH-C 18:0 | 0.4% |
| FA C 16:0 | 0.2% |
| FA C 16:1 | 0.2% |
| FA C 18:0 | 0.1% |
| FA C 18:1 | 1.1% |
| Others | 0.3% |

EXAMPLE 2

To produce the biosurfactants in a bioreactor ($V_{tot}$=2.5 l), 2 l of a culture medium of the following composition are introduced:

| | |
|---|---|
| Glucose.H$_2$O | 140.00 g/l |
| Sodium citrate.3 H$_2$O | 5.00 g/l |
| Yeast extract (granulated, Merck, Darmstadt) | 4.00 g/l |
| Ammonium chloride | 1.54 g/l |
| Potassium dihydrogen phosphate | 1.00 g/l |
| Magnesium sulfate.7 H$_2$O | 0.70 g/l |
| Sodium chloride | 0.50 g/l |
| Calcium chloride.2 H$_2$O | 0.27 g/l |
| Dipotassium hydrogen phosphate.3 H$_2$O | 0.16 g/l |

The medium is inoculated with the yeast *Candida bombicola* ATCC 22214 and incubated under the stated conditions for 40 h until the biomass has completely developed (18 g/l). After growth is complete, 1.5 g/l 1-dodecanol is fed in under sterile conditions through a metering pump. The yeast culture responds to the addition with a spontaneous reduction in the dissolved oxygen concentration from the previous 75 to 10% pO$_2$. At the same time there are significant increases in the rate of carbon dioxide formation and the rate of oxygen consumption. After addition of a further 2 g/l 1-dodecanol, about 30 h elapse until the added fatty alcohol is completely metabolized. The depletion of the substance leads to a renewed rise in the dissolved oxygen concentration and a reduction in the rates of oxygen consumption and carbon dioxide formation before, owing to further addition of 1-dodecanol, the conditions are restored to those before metabolization was complete. The cultivation is continued with multiple repetition of such dodecanol additions until it is stopped. After a cultivation time of 160 h, 50 g/l of glucose in solid, nonsterile form is metered in in order to prevent limitation of this energy source. As little as 25 h after the first metering in of the alcohol it is possible to detect the novel sophorose lipid in the culture broth by the HPLC technique. Its concentration increases to 14.3 g/l (corresponding to 0.64 g per g of 1-dodecanol) by the end of the cultivation. In addition, the pH of the culture suspension decreases over the entire product formation period. After a cultivation period of 235 h, a total amount of 22.5 g/l of the alcohol has been converted, and the cultivation is then stopped. FIG. 1 summarizes the progress of the bioreactor cultivation on the basis of all the analytical parameters.

In FIG. 1, DBM means dry biomass, SL means sophorose lipid, Q CO$_2$ means the rate of carbon dioxide formation, Q O$_2$ means the rate of oxygen consumption, R Q means the respiratory quotient and pO$_2$ means the oxygen partial pressure indicated as percentage of the saturation value.

To isolate the products, the culture suspension is neutralized with 1 N sodium hydroxide solution and then extracted twice with twice the volume of ethyl acetate. The organic phases are separated off, combined and dried over anhydrous sodium sulfate. After removal of the desiccant on a paper filter, the solvent is distilled off under reduced pressure in a rotary evaporator. The crude glycolipid product is obtained in a total yield of 14.3 g/l.

Investigations by thin-layer chromatography on silylated silica gel (RP-18) in the eluent mixture methanol/water 90:10 (v/v) show that the product mixture consists of the compounds described above in Example 1.

EXAMPLE 3

For basic hydrolysis of the sophorose lipid obtained in Example 2, 20 g of the glycolipid mixture are dissolved in 400 ml of 1 N sodium hydroxide solution and refluxed with stirring for 4 h.

Subsequently, the reaction solution is adjusted to pH 4 with concentrated hydrochloric acid and cooled to 4° C. for 12 h. The precipitate which separates out is removed on a paper filter, washed with 500 ml of ice-cold water and again taken up in 300 ml of water for recrystallization (60° C.→4° C.). The precipitated product is again removed by filtration and is then freeze dried. The solid can be separated into two substances by chromatography on silylated silica gel (RP-18) in the eluent system methanol/water 80:20 (v/v). Spectroscopic investigations on the fractionated substances prove that the less polar main component has the structure of Compound 2 (molecular structure 2b). The more polar component is the deacetylated sophorose lipid predominantly with free 17-hydroxyoctadecenoic acid as hydrophobic component of the molecule.

R$_f$ (RP-18: methanol/water 90:10 v/v): 0.54 [Compound 2]

Srectroscoiic Data for Compound 2

MS (FAB, matrix glycerol, neg.):

m/z=509 (100, [M−H]$^-$), 347 (10, [M−glucose+H$_2$O−H]$^-$)

EXAMPLE 4

To produce the alkyl sophorosides from 2-, 3- and 4-dodecanone and 4-tetradecanol, 100 ml of a culture medium of the following composition are introduced into each 500 ml Erlenmeyer flask with baffles:

| | |
|---|---|
| Glucose.H$_2$O | 150.00 g/l |
| Sodium citrate.3 H$_2$O | 5.00 g/l |
| Yeast extract | 4.00 g/l |
| Ammonium chloride | 1.54 g/l |
| Potassium dihydrogen phosphate | 1.00 g/l |
| Magnesium sulfate.7 H$_2$O | 0.70 g/l |
| Sodium chloride | 0.50 g/l |
| Calcium chloride.2 H$_2$O | 0.27 g/l |
| Dipotassium hydrogen phosphate.3 H$_2$O | 0.16 g/l |

The medium is inoculated with the yeast *Candida bombicola* ATCC 22214 and incubated on a rotary shaker at 100 rpm at a temperature of 30° C. After a cultivation time of 48, 72 and 96 h, in each case 3.3 g/l of the various hydrophobic C substrates are added (total amount 10 g/l) under aseptic conditions to the culture solution. The culture is carried out under unchanged conditions between and after the additions of the substrates. The pH of the culture suspension decreases over the entire range of cultivation. After a cultivation period of 12 d, the supplied amounts of 2- and 3-dodecanone and 4-tetradecanol have been converted completely; residues of substrate remain in the culture broth of the 4-dodecanone cultivation. All the cultivations are then stopped.

To isolate the products, the culture suspensions are neutralized with 1 N sodium hydroxide solution and then extracted twice with twice the volume of ethyl acetate. The organic phases are separated off, combined and dried over anhydrous sodium sulfate. After removal of the desiccant on a paper filter, the solvent is removed by distillation under reduced pressure in a rotary evaporator. To remove residues of substrate, the product of the 4-dodecanone cultivation is repeatedly washed with hexane. The remaining precursor-free and highly viscous crude products are mixed with n-butanol for azeotropic removal of the bound water. It is subsequently completely removed by distillation again under reduced pressure. The product mixtures are obtained in the following yields:

| | | |
|---|---|---|
| 2-Dodecanone: | 14 g/l | corresponding to 1.4 g per g of 2-dodecanone |
| 3-Dodecanone: | 17 g/l | corresponding to 1.7 g per g of 3-dodecanone |
| 4-Dodecanone: | 3 g/l | corresponding to 0.3 g per g of 4-dodecanone |
| 4-Tetradecanol: | 17 g/l | corresponding to 1.7 g per g of 4-tetradecanol |

They contain, determined by GC-MS, 2-, 3- and 4-alkanols homologous with the substrates as lipid components in addition to more or less small amounts of hydroxy fatty acids.

| Glycolipid mixture based on glucose/2-dodecanone | |
|---|---|
| 2-dodecanol | 84.5% |
| FA 15-OH-C 16:0 | 0.3% |
| FA 16-OH-C 16:0 | 0.3% |
| FA 17-OH-C 18:1 | 4.1% |
| FA 17-OH-C 18:0 | 2.2% |
| FA 18-OH-C 18:1 | 0.6% |
| FA C 16:0 | 0.9% |
| FA C 16:1 | 0.5% |
| FA C 18:1 | 5.0% |
| FA C 18:0 | 0.7% |
| Others | 0.9% |
| Glycolipid mixture based on glucose/3-dodecanone: | |
| 3-dodecanol | 80.0% |
| 2-undecanol | 3.4% |
| FA 15-OH-C 16:0 | 0.6% |
| FA 16-OH-C 16:0 | 0.7% |
| FA 17-OH-C 18:1 | 7.5% |
| FA 17-OH-C 18:0 | 2.5% |
| FA 18-OH-C 18:1 | 1.2% |
| FA 18-OH-C 18:0 | 0.2% |
| FA C 16:0 | 0.3% |
| FA C 16:1 | 0.3% |
| FA C 18:1 | 2.6% |
| FA C 18:0 | 0.3% |
| Others | 0.4% |
| Glycolipid mixture based on glucose/4-dodecanone: | |
| 4-dodecanol | 41.5% |
| Other C12 | 22.0% |
| FA 15-OH-C 16:0 | 1.4% |
| FA 16-OH-C 16:0 | 1.1% |
| FA 17-OH-C 18:1 | 12.6% |
| FA 17-OH-C 18:0 | 1.6% |
| FA 18-OH-C 18:1 | 0.3% |
| FA C 16:0 | 0.9% |
| FA C 16:1 | 1.3% |
| FA C 18:0 | 0.3% |
| FA C 18:1 | 3.7% |
| Others | 8.4% |
| Glycolipid mixture based on glucose/4-tetradecanol: | |
| 4-Tetradecanol | 23.8% |
| FA 15-OH-C 16:0 | 4.7% |
| FA 16-OH-C 16:0 | 4.8% |
| FA 17-OH-C 18:1 | 39.9% |
| FA 17-OH-C 18:0 | 17.4% |
| FA 18-OH-C 18:1 | 6.5% |
| FA 18-OH-C 18:0 | 1.1% |
| Others | 1.8% |

EXAMPLE 5

The sophorose lipid obtained in Example 4 from 2-dodecanone was used to determine the enantiomeric excess of the fatty alcohol. The 2-dodecanol was obtained from the sophorose lipid by liberation by acidic methanolysis. The enantiomeric excess was determined by measuring the optical rotation of the isolated 2-dodecanol at 25° C. and a wavelength of 589 nm. The optical rotation $[\alpha]^{25}_{589}$ is +7.4° (5 g/100 ml measured in ethanol) [←c=5].

The optical rotation stated in the literature for (S)-2-dodecanol is +6.9° (5 g/100 ml measured in ethanol at 25° C.) (Kirchner et al., J. Am. Chem. Soc., 107, (1985), 7072–7076). According to the author's statements, this corresponds to an enantiomeric excess of 95%. It is evident from this that the enantiomeric excess of the 2-dodecanol according to the invention ought to be considerably greater than 95%.

What is claimed is:

1. A sophorose lipid of the formula I

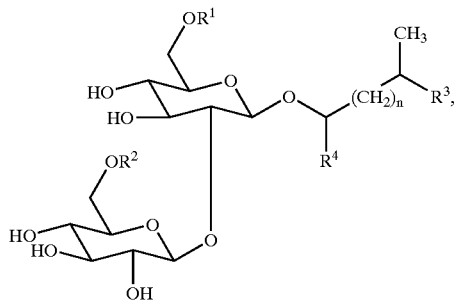

$R^4$ is H, —$CH_2CH_3$ or —$CH_2CH_2CH_3$, n is an integer from 8 to 27, $R^1$ and $R^2$ are, independently of one another, H or acetyl and $R^3$ is H or —OH.

2. A sophorose lipid as claimed in claim 1, wherein n is an integer from 8 to 14.

3. The sophorose lipid as claimed in claim 1, wherein n is an integer from 8 to 12.

4. A method for producing sophorose lipids according to the formula I,

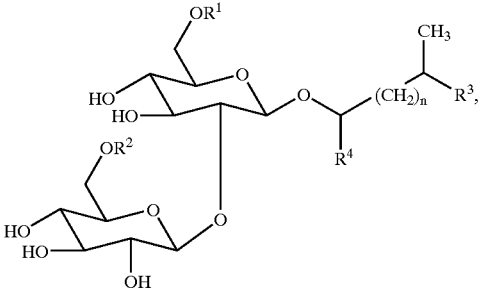

$R^1$ and $R^2$ are, independently of one another, H or acetyl $R^3$ is H or —OH, n is an integer from 8 to 27, and $R^4$ is —$CH_3$, —$CH_2CH_3$ or —$CH_2CH_2CH_3$, in which a yeast with the ability to secrete sophorose lipids in the form of a lactone into the culture supernatant is fermented in a culture medium which contains glycerol, succinate, a mono-, a di- and/or a trisaccharide and a lipid precursor, and then the sophorose lipid is isolated from the culture solution, wherein the lipid precursor comprises one or more 3-alkanols, 4-alkanols or alkanones with a chain length of from 6 to 30 carbon atoms or mixtures of these alkanols/alkanones.

5. The method as claimed in claim 4, wherein the chain length of the alkanol/alkanone is 10 to 18 carbon atoms.

6. The method as claimed in claim 4, wherein said alkanone is a 2-alkanone, a 3-alkanone, a 4-alkanone or mixtures thereof.

7. The method as claimed in claim 4, wherein said alkanone is 2-dodecanone or 3-dodecanone.

8. The method as claimed in claim 4, wherein said yeast is a fermented yeast of Candida.

9. The method as claimed in claim 8, wherein said Candida is *Candida bombicola, Candida bogoriensis, Candida magnoliae, Candida gropengiesseri* or *Candida apicola*.

10. The method as claimed in claim 4, wherein said saccharide is glucose or sucrose.

11. A method for producing sophorose lipids according to the formula I,

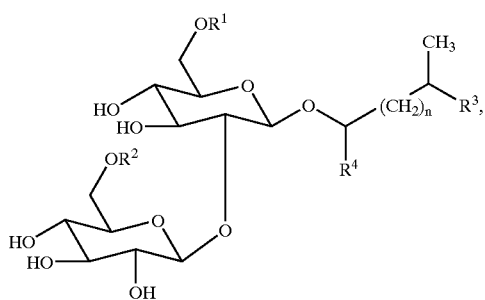

$R^1$ and $R^2$ are, independently of one another, H or acetyl $R^3$ is H or —OH, n is an integer from 8 to 27, and $R^4$ is H, —$CH_3$, —$CH_2CH_3$ or —$CH_2CH_2CH_3$, in which a yeast with the ability to secrete sophorose lipids in the form of a lactone into the culture supernatant is fermented in a culture medium which contains glycerol, succinate, a mono-, a di- and/or a trisaccharide and a lipid precursor, and then the sophorose lipid is isolated from the culture solution, wherein the lipid precursor comprises one or more alkanols, alkanals or alkanones with a chain length of from 6 to 30 carbon atoms or mixtures of these alkanols/alkanals alkanones, and the culture medium is kept under a reduced oxygen concentration during the fermentation.

12. The method as claimed in claim 11, wherein the oxygen partial pressure of the culture solution is less than 40% of the saturation value.

13. The method as claimed in claim 12, wherein the oxygen partial pressure of the culture solution is less than 15% of the saturation value.

14. The method as claimed in claim 11, wherein said lipid precursor is a 1-alkanol or an alkanal.

15. The method as claimed in claim 11, wherein said alkanol is 1-dodecanol.

* * * * *